(12) United States Patent
Murata et al.

(10) Patent No.: US 11,045,508 B2
(45) Date of Patent: Jun. 29, 2021

(54) COMPOSITION FOR PREVENTING OR IMPROVING IMPAIRED RENAL FUNCTION, PHARMACEUTICAL COMPOSITION, FOOD/BEVERAGE COMPOSITION, AND METHOD OF PREVENTING OR IMPROVING IMPAIRED RENAL FUNCTION USING THE COMPOSITION FOR PREVENTING OR IMPROVING IMPAIRED RENAL FUNCTION

(71) Applicant: MORINAGA MILK INDUSTRY CO., LTD., Tokyo (JP)

(72) Inventors: Mai Murata, Kanagawa (JP); Junichi Minami, Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 16/394,330

(22) Filed: Apr. 25, 2019

(65) Prior Publication Data

US 2020/0338140 A1  Oct. 29, 2020

(51) Int. Cl.
| | | |
|---|---|---|
| A61K 35/745 | (2015.01) | |
| A61K 9/00 | (2006.01) | |
| A61P 13/12 | (2006.01) | |
| C12N 1/20 | (2006.01) | |
| A23L 33/135 | (2016.01) | |
| A23C 9/12 | (2006.01) | |
| C12R 1/01 | (2006.01) | |
| A23C 9/16 | (2006.01) | |

(52) U.S. Cl.
CPC .......... *A61K 35/745* (2013.01); *A23C 9/1203* (2013.01); *A23C 9/16* (2013.01); *A23L 33/135* (2016.08); *A61K 9/0053* (2013.01); *A61K 9/0095* (2013.01); *A61P 13/12* (2018.01); *C12N 1/20* (2013.01); *C12R 1/01* (2013.01); *A23V 2002/00* (2013.01); *A23Y 2300/29* (2013.01)

(58) Field of Classification Search
CPC .. A61K 35/745; A61K 9/0053; A61K 9/0095; A23Y 2300/29; A61P 13/12; A23L 33/135; A23L 2/66; A23L 33/125; A23L 33/15; A23L 33/16; A23L 33/115; A23L 33/19; A23L 33/21; A23L 2/52; C12N 1/20; A23C 9/1203; A23C 9/16; C12R 1/01; A23V 2002/00
See application file for complete search history.

(56) References Cited

PUBLICATIONS

Koppe et al., "Probiotics and chronic kidney disease," Kidney International, 2015, 88, 958-966, cited in 112 rejection (Year: 2015).*

National Institute of Diabetes and Digestive and Kidney Diseases webpage, edited Oct. 2016, accessed Aug. 12, 2020, https://www.niddk.nih.gov/health-information/kidney-disease/chronic-kidney-disease-ckd/prevention, cited in 112 rejection (Year: 2016).*

Nakabayashi et al, "Effects of synbiotic treatment on serum level of p-creson in haemodialysis pateints: a preliminary study" Nephrol Dial. Transplant, 2011, 26: 1094-1098, cited as relevant prior art (Year: 2011).*

Dehghani et al, "Synbiotic Supplementations for Azotemia in Patients with Chronic Kidney Disease," Iranian Journal of Kidney Diseases, vol. 10, No. 6, Nov. 2016, cited in 102 and 103 rejection (Year: 2016).*

* cited by examiner

*Primary Examiner* — Kade Ariani

(74) *Attorney, Agent, or Firm* — Cermak Nakajima & McGowan LLP; Shelly Guest Cermak

(57) ABSTRACT

Provided is a composition for preventing or improving impaired renal function, containing *Bifidobacterium breve* as an active ingredient. The composition for preventing or improving impaired renal function is capable of reducing blood creatinine levels. The composition for preventing or improving impaired renal function can also be used in a pharmaceutical composition or a food or beverage product composition.

10 Claims, No Drawings

COMPOSITION FOR PREVENTING OR IMPROVING IMPAIRED RENAL FUNCTION, PHARMACEUTICAL COMPOSITION, FOOD/BEVERAGE COMPOSITION, AND METHOD OF PREVENTING OR IMPROVING IMPAIRED RENAL FUNCTION USING THE COMPOSITION FOR PREVENTING OR IMPROVING IMPAIRED RENAL FUNCTION

TECHNICAL FIELD

The present technology pertains to a composition for preventing or improving impaired renal function, a pharmaceutical composition and a food or beverage product composition using said composition for preventing or improving impaired renal function, and a method of preventing or improving impaired renal function.

BACKGROUND ART

Apart from acute nephritis and the like, kidney disease is a lifelong illness, and can ultimately become end-stage renal failure (a condition requiring dialysis therapy). Because the kidneys have considerable amounts of reserve strength, chronic renal impairment is substantially asymptomatic until kidney function reaches 20% or less. In other words, there is a high potential of already having end-stage renal failure by the time symptoms of some sort appear, and symptoms often have already progressed to the point that dialysis is necessary.

The number of chronic dialysis patients is estimated at around 200,000, and 3,000 new patients are said to begin dialysis every year. In the case of chronic kidney disease (CKD), the goal is to delay the progress of the disease and prolong kidney function as much as possible; no method of treating the disease itself exists. The current state of affairs is to suppress the progress of disease via diet therapy or pharmacotherapy for renal failure, and prolong the remaining function of the kidneys.

In the face of these circumstances, there has long been a demand for the development of drugs and compositions that have the effect of preventing or improving impaired renal function.

In response, Patent Document 1, for example, discloses an agent for improving renal function containing a specific synthetic compound. Patent Document 2 discloses a composition for increasing renal function that reduces creatinine and BUN levels in a subject, the composition containing a specific kind of probiotic bacteria.

Patent Literature

Patent Document 1: JP 2011-509941 A
Patent Document 2: JP 2013-209396 A

SUMMARY

As discussed above, various methods for preventing or treating impaired renal function have been proposed in the past. However, methods using synthetic compounds or the like, as in Patent Document 1, bear the risk of side effects. A number of methods of preventing or treating impaired renal function through the consumption of probiotic bacteria or fermentation products, as in Patent Document 2, have already been promoted, probiotics are known to exhibit different physiological effects depending on strain, and universal results have not been obtained.

Thus, a primary aspect of the present invention is to provide a novel composition for preventing or improving impaired renal function.

It is an aspect of the present invention to provide a composition for preventing or improving impaired renal function, containing *Bifidobacterium breve* as an active ingredient.

It is an aspect of the present invention to provide the composition as described above, wherein the *Bifidobacterium breve* is *Bifidobacterium breve* MCC1274 (FERM BP-11175).

It is an aspect of the present invention to provide the composition as described above, wherein the composition improves glomerular function.

It is an aspect of the present invention to provide the composition as described above, wherein the composition reduces blood creatinine level.

It is an aspect of the present invention to provide the composition as described above, wherein the composition is a pharmaceutical composition.

It is an aspect of the present invention to provide the composition as described above, wherein the composition is a food or beverage product composition.

It is an aspect of the present invention to provide the composition as described above, containing $10^6$ to $10^{12}$ cfu *Bifidobacterium breve* MCC1274 (FERM BP-11175) per packaged unit.

It is an aspect of the present invention to provide the composition as described above, containing $10^6$ to $10^{12}$ cfu *Bifidobacterium breve* MCC1274 (FERM BP-11175) per meal.

It is an aspect of the present invention to provide the composition as described above, wherein the composition is fermented milk.

It is an aspect of the present invention to provide a use of *Bifidobacterium breve* in an agent for preventing or improving impaired renal function, a pharmaceutical for preventing or improving impaired renal function, or a food or beverage product for preventing or improving impaired renal function.

It is an aspect of the present invention to provide the use as described above, wherein the *Bifidobacterium breve* is *Bifidobacterium breve* MCC1274 (FERM BP-11175).

A method of preventing or improving impaired renal function, the method including administering *Bifidobacterium breve* to a subject.

It is an aspect of the present invention to provide the use as described above, wherein the *Bifidobacterium breve* is *Bifidobacterium breve* MCC1274 (FERM BP-11175). Specifically, the present technology provides, firstly, a composition for preventing or improving impaired renal function, containing *Bifidobacterium breve* as an active ingredient.

The *Bifidobacterium breve* can be *Bifidobacterium breve* MCC1274 (FERM BP-11175).

The composition can be one for improving glomerular function.

The composition can also be one for reducing blood creatinine levels.

The composition can also be used as a pharmaceutical composition or a food or beverage product composition.

The present technology also provides a use of *Bifidobacterium breve* in an agent for preventing or improving impaired renal function, a pharmaceutical for preventing or improving impaired renal function, or a food or beverage product for preventing or improving impaired renal function.

The *Bifidobacterium breve* can be *Bifidobacterium breve* MCC1274 (FERM BP-11175).

The present technology also provides a method of preventing or improving impaired renal function, the method including administering *Bifidobacterium breve* to a subject.

The *Bifidobacterium breve* can be *Bifidobacterium breve* MCC1274 (FERM BP-11175).

In accordance with the present technology, it is possible to provide a novel composition for preventing or improving impaired renal function.

The effects listed here are not necessarily limited, and may be any effect disclosed herein.

DETAILED DESCRIPTION

Embodiments for carrying out the present invention will be described hereafter.

The embodiments described hereafter are merely examples of representative embodiments of the present invention, and the scope of the present invention will not be narrowly construed on the basis thereof 1. Composition for Preventing or Improving Impaired Renal Function The composition for preventing or improving impaired renal function is characterized by containing *Bifidobacterium breve* as an active ingredient.

*Bifidobacterium breve* is one species in genus *Bifidobacterium*. *Bifidobacterium breve* primarily lives in large numbers in the colons of infants, and, of the various species in genus *Bifidobacterium*, is known along with *Bifidobacterium longum* subsp. *infantis* and the like as infantile *Bifidobacterium* bacteria.

Because the active ingredient of the composition for preventing or improving impaired renal function is *Bifidobacterium breve*, which primarily lives in large numbers in the colons of infants, the composition has superior safety, with little fear of side effects even when administered for extended periods of time, and thus is extremely useful. The composition is also highly safe when used in conjunction with other drugs.

Examples of strains of *Bifidobacterium breve* include *Bifidobacterium breve* MCC1274 (FERM BP-11175), M-16V (NITE BP-02622), UCC2003, YIT4010, YIT4064, BBG-001, BR-03, B632 (DSMZ 24706), C50, Bb99 (DSM 13692), R0070, ATCC15700, ATCC15698, DSM 24732, and the like; of these, it is preferable to use *Bifidobacterium breve* MCC1274 (FERM BP-11175).

MCC1274 was deposited with the International Patent Organism Depository of the National Institute of Advanced Industrial Science and Technology (Central No. 6, 1-1-1 Higashi, Tsukuba, Ibaraki Prefecture, 305-8566, Japan) (presently, IPOD, the International Patent Organism Depository of the National Institute of Technology and Evaluation (NITE-IPOD): Room 120, 2-5-8 Kazusakamatari, Kisarazu, Chiba Prefecture, 292-0818, Japan) on Aug. 25, 2009, with the accession number IPOD FERM BP-11175.

The strains identified by the examples of strain names listed above are not limited to strains deposited or registered with specific organizations under those strain names (hereafter also referred to as "deposited strains" for convenience of explanation), but also include strains that are substantially the same (also referred to as "derived strains" or "induced strains"). In other words, "*Bifidobacterium breve* MCC1274 (FERM BP-11175)", for example, is not limited to the strain deposited at the abovementioned depository institution with the accession number MCC1274 (FERM BP-11175), but also includes strains that are substantially the same. As used in connection with strains, the expression "substantially the same as the deposited strain) refers to strains that belong to the same species as the deposited strain and yield the effect of preventing or improving impaired renal function that is the effect. A strain that is substantially the same as the deposited strain may be, for example, a derived strain for which the deposited strain is the parent strain. Examples of derived strains include strains bred from the deposited strain and strains naturally developing from the deposited strain. Examples of strains and derived strains that are substantially the same include the following.

(1) Strains identified as being identical strains via RAPD (randomly amplified polymorphic DNA) or PFGE (pulsed-field gel electrophoresis) (disclosed on page 43, Probiotics in Food: Health and Nutritional Properties and Guidelines for Evaluation 85).

(2) Strains that retain only genes from the deposited strain, have no exogenous genes, and have 95% or higher DNA identity.

(3) Strains bred from the strain (including modified via genetic engineering, spontaneous mutations, and natural spontaneous mutations).

The term "impaired renal function" includes various types of kidney disease associated with impairment of kidney function, and refers to a state that is caused by acute nephritis or chronic nephritis, or by diabetes, gout, drug side effects, or the like, and in which symptoms such as reduced kidney filtration functioning or abnormal intracorporeal circulation are present. Examples of such kidney diseases include various types of glomerular disease (acute nephritic syndrome, rapidly progressive nephritic syndrome, iterative (recurrent) or persistent hematuria, chronic nephritic syndrome, nephrotic syndrome, genetic nephropathy, diffuse glomerulonephritis, dense deposit disease, etc.), tubulointerstitial nephritis, renal failure, and kidney stones and urinary stones. In morphological types of glomerular disease, examples include primary glomerular disease (minimal change, focal glomerulosclerosis, membranous nephropathy, mesangial proliferative glomerulonephritis (IgA nephropathy, non-IgA nephropathy), membranoproliferative glomerulonephritis, diffuse sclerosing glomerulonephritis, etc.). Examples of kidney disease based on systemic disease include renal collagen disease (renal scleroderma, lupus nephritis, etc.), diabetic nephropathy, renal amyloidosis, purpura nephritis, renal gout, genetic kidney disease (genetic nephritis, Alport syndrome, Fabry disease, etc.), and the like. The composition for preventing or improving impaired renal function can be used to prevent or improve these and other primary and secondary kidney diseases (including glomerular lesions in kidney transplants).

Impaired renal function can be evaluated via blood creatinine level (also referred to as "serum creatinine level"), blood urea nitrogen (BUN), creatinine clearance, or the like. Kidney function can also be evaluated via estimated glomerular filtration rate (eGFR) as calculated from sex, age, and blood creatinine level.

The term "improve" means improvement in disease, symptoms, or state; prevention or slowing of aggravation of disease, symptoms, or state; and reversal, prevention, or slowing of progress of disease or symptoms. "Prevent" refers to prevention or slowing of the onset of disease or symptoms in the receiving subject, or reducing the risk of disease or symptoms in the receiving subject.

Specific symptoms of impaired renal function include, in particular, reduced glomerular function and increased blood creatinine level. The glomeruli are the core of kidney function, and the glomerular filtration rate (GFR), which indicates how well they are working, is known to be an index reflecting kidney function. When GFR decreases due to reduced glomerular function, sufficient excretion of metabolic products and the like becomes impossible. Creatinine is a waste product of proteins in the muscles that is normally filtered out in the kidneys by the glomeruli and excreted in the urine; however, when kidney function decreases, the amount thereof excreted in the urine decreases, and creatinine accumulates in the blood. Accordingly, it is known that blood creatinine levels increase when kidney function decreases. The composition for preventing or improving impaired renal function is effective against reductions in glomerular function and diminished blood creatinine levels, and, in particular, is effective against diminished blood creatinine levels, as will be shown in the examples described hereafter.

There is no particular limitation upon the subject receiving the composition for preventing or improving impaired renal function; the composition can be applied to animals including humans. There is also no particular limitation upon the sex, age, etc., of the recipient. Thanks to its high level of safety, the composition for preventing or improving impaired renal function can also be used on infants and children, pregnant, perinatal, and nursing women, and elderly or sick individuals with high risk of reduced kidney function.

As the *Bifidobacterium breve* MCC1274 (FERM BP-11175) constituting its active ingredient, the composition for preventing or improving impaired renal function may contain a culture containing *Bifidobacterium breve* MCC1274 (FERM BP-11175).

There is no particular limitation on the medium used to culture the *Bifidobacterium breve*; a medium ordinarily used to culture bacteria of genus *Bifidobacterium* can be used.

Sugars such as glucose, galactose, lactose, arabinose, mannose, sucrose, starch, starch hydrolysate, and molasses can be used as carbon sources according to assimilability. Ammonium salts and nitrates such as ammonia, ammonium sulfate, ammonium chloride, and ammonium nitrate can be used as nitrogen sources. Sodium chloride, potassium chloride, potassium phosphate, magnesium sulfate, calcium chloride, calcium nitrate, manganese chloride, iron(II) sulfate, and the like can be used as an inorganic salt. Organic components such as peptone, soy flour, defatted soy flour, meat extract, and yeast extract may also be used.

There is no particular limitation upon culturing conditions as long as the effects are not lost; for example, culturing temperature is ordinarily 25-50° C., preferably 35-42° C. Culturing is preferably performing in anaerobic conditions; for example, culturing can be performed while passing an anaerobic gas such as carbon dioxide gas through the culture. Culturing may also be performed in microaerophilic conditions, such as in a liquid static culture.

For the *Bifidobacterium breve*, the obtained culture may be used as-is after culturing, or diluted or concentrated, or bacteria recovered from the culture may be used. As used herein, the term "culture" includes culture supernatant.

For the bacteria, the obtained culture may be used as-is after culturing, or diluted or concentrated, or bacteria recovered from the culture may be used. Various types of additional operations such as heating and freeze-drying can also be performed after culturing as long as the effects are not lost. The bacteria may be live or dead. If live, the bacteria are preferably processed via solution freezing, spray-drying, freeze-drying, or an oil drop method. Examples of dead bacteria include bacteria that have been killed via heating, freeze-drying, or the like.

Examples of other methods of preparing dead bacteria include spray-drying, retort sterilization, freeze-drying, UHT sterilization, pressure sterilization, high-pressure steam sterilization, dry heat sterilization, free-flowing steam sterilization, electromagnetic sterilization, electron beam sterilization, radio frequency sterilization, irradiative sterilization, ultraviolet sterilization, ethylene oxide gas sterilization, hydrogen peroxide gas plasma sterilization, and chemical sterilization (alcohol sterilization, formalin fixation, electrolyzed water treatment). The bacteria may be crushed. The crushed bacteria may be obtained by crushing live bacteria or dead bacteria, and may be heated, freeze-dried, or the like after crushing. Crushing using methods and instruments known in the art, such as physical crushing, enzymatic dissolution, chemical processing, autolytic processing, or the like can be selected.

Physical crushing may be performed via processing in a liquid bacteria suspension or processing powdered bacteria. Examples of physical crushing that can be selected include agitation-based crushing using an ultrasonic homogenizer, homogenizer, ball mill, bead mill, dyno mill, planetary mill, or the like; pressure-based crushing using a jet mill, french press, cell crusher, or the like; and crushing by damaging cells via filter filtration. One possible example of enzymatic dissolution is to break down the cellular structure of the bacteria using an enzyme such as lysozyme. One possible example of chemical processing is to break down the cellular structure of the bacteria using a surfactant such as soybean phospholipids, glycerin fatty acid ester, or the like. One possible example of autolytic processing is to use the enzymes of certain lactic acid bacteria to dissolve those bacteria. Physical crushing is preferable as there is no need to add other chemicals or compounds.

The composition for preventing or improving impaired renal function may consist solely of the active ingredient, or may be a composition containing the active ingredient and an optional component other than the active ingredient. There is no particular limitation upon optional components as long as the effects are not lost; additives normally included in pharmaceuticals (such as the formulation carriers described hereafter) can be included.

2. Specific Forms of the Composition for Preventing or Improving Impaired Renal Function The composition for preventing or improving impaired renal function can be used in various forms, such as a food or beverage product, pharmaceutical, quasi drug, animal feed, or the like.

The purpose of the form may be use for therapeutic purposes or use for non-therapeutic purposes. The term "non-therapeutic purposes" does not include medical intervention, i.e., treatment of the human body via therapy; examples include promoting health, cosmetic treatment, and the like.

<Food or Beverage Product>

A food or beverage product composition using the composition for preventing or improving impaired renal function (hereafter also referred to as "the food or beverage product composition") can be prepared by adding the composition to a known food or beverage product, or the composition can be mixed into the raw materials of a food or beverage product to produce a new food or beverage product.

The food or beverage product composition may be in any form, such as liquid, paste, solid, or powdered; and may be tablets, a liquid diet, or other forms such as wheat flour products, instant food product, processed agricultural products, processed aquatic products, processed livestock products, milk and dairy products, oils and fats, basic seasonings, composite seasonings and food products, frozen food products, sweets and snacks, beverages, and other commercial products.

Examples of wheat flour products include bread, macaroni, spaghetti, noodles, cake mix, deep frying breading, and breadcrumbs.

Examples of instant food products include instant noodles, cup noodles, retort pouch food products, canned goods, microwave food products, instant soups and stews, instant miso soup and Japanese clear soup, canned soup, freeze-dried food products, and other instant food products.

Examples of processed agricultural products include canned agricultural products, canned fruit, jams and marmalades, pickles, cooked beans, dried agricultural products, and cereals (processed grain products).

Examples of processed aquatic products include canned aquatic products, fish ham or sausage, fish paste products, marine delicacies, and tsukudani.

Examples of processed animal husbandry products include canned animal husbandry products, paste, and livestock ham and sausage.

Examples of milk and dairy products include fermented milk products such as yogurt, processed milk, milk beverages, lactic acid bacteria beverages, cheese, ice cream, prepared powdered milk, cream, powdered milk preparations for children, infant nutritional supplements, milk for pregnant or nursing women, and other dairy products.

Examples of oils and fats include butter and margarine, vegetable oils, and the like.

Examples of basic seasonings include soy sauce, miso, sauces, processed tomato seasonings, mirin, and vinegar; and examples of composite seasonings and food products include cooking mixes, curry bases, dipping sauces, dressings, noodle soup bases, spices, and other composite seasonings.

Examples of frozen food products include frozen raw ingredients, frozen partially cooked food products, and frozen cooked food products.

Examples of sweets and snacks include caramels, candies, chewing gum, chocolate, cookies, biscuits, cakes, pies, snacks, crackers, Japanese confections, rice crackers, bean crackers, desserts, and other sweets and snacks.

Examples of beverages include carbonated beverages, natural fruit juice, fruit juice beverages, fruit-juice-contained soft drinks, fruit pulp beverages, fruit beverages with fruit particles, vegetable-based beverages, soy milk, soy milk beverages, coffee beverages, tea beverages, powdered beverages, concentrated beverages, sports beverages, nutritional beverages, alcoholic beverages, and other beverages drunk for enjoyment.

Examples of other commercial food products include baby food, rice seasoning, and ochazuke non.

The food or beverage product composition can be produced by adding the bacteria to the ingredients of an ordinary food or beverage product, and can be produced in the same manner as an ordinary food or beverage product apart from the addition of the bacteria. The bacteria may be added during any stage of the process of manufacturing the food or beverage product composition. The food or beverage product composition may also be produced via a fermentation process affected by the added bacteria. Examples of such food or beverage product compositions include lactic acid bacteria beverages, fermented milk, etc.

Ingredients used in ordinary food or beverage products can be used as the ingredients of the food or beverage product composition. The produced food or beverage product composition can be consumed orally.

It is also possible, for example, to add the bacteria to expressed mother's milk and orally feed to a newborn or infant, or to administer using a nasogastric feeding tube or the like.

Ingredients having probiotic effects and ingredients that support probiotic effects, both known and those discovered in the future, can be used in the food or beverage product composition as long as the effects are not negatively affected.

Specifically, for example, ingredients such as proteins, such as whey protein, casein protein, soy protein, and pea protein, as well as mixtures and hydrolysates thereof; amino acids such as leucine, valine isoleucine, and glutamine; vitamins such as vitamin B6 and vitamin C; creatine; citric acid; fish oil; and oligosaccharides such as isomaltooligosaccharide, galactooligosaccharides, xylooligosaccharides, soy oligosaccharides, fructooligosaccharides, lactulose, and human milk oligosaccharides (HMOs) can be mixed with the bacteria to produce the composition.

Examples of human milk oligosaccharides include neutral human milk oligosaccharides such as 2'-fucosyllactose, 3-fucosyllactose, 2', 3-difucosyllactose, lacto-N-triose II, lacto-N-tetraose, lacto-N-neotetraose, lacto-N-fucopentaose I, lacto-N-neofucopentaose, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose, and lacto-N-neohexaose; and acidic human milk oligosaccharides such as 3'-sialyllactose, 6'-sialyllactose, 3-fucosyl-3'-sialyllactose, and disialyl-lacto-N-tetraose.

The *Bifidobacterium breve* MCC1274 (FERM BP-11175) content of the food or beverage product composition may be freely set as long as the effects are not negatively affected. The *Bifidobacterium breve* MCC1274 (FERM BP-11175) content of the food or beverage product composition is especially preferably $1\times10^3$ to $1\times10^{12}$ cfu/g. The daily dosage is at least $1\times10^3$ cfu/day, more preferably $1\times10^6$ cfu/day, more preferably $1\times10^8$ cfu/day, more preferably $2\times10^{10}$ cfu/day or more. It is especially preferable that one meal contain $10^6$ to $10^{12}$ cfu of *Bifidobacterium breve* MCC1274 (FERM BP-11175). "Cfu" represents "colony forming unit". If the bacteria are dead, cfu/g or cfu/ml can be replaced by cells/g or cells/ml. If the bacteria are crushed, the weight as calculated from the number of bacteria (cells/g) before crushing can be used.

Foods for Special Dietary Uses

The composition can be applied to a health-promoting food or a food for special dietary uses. For the sake of conforming with internal and external trends and the existing Japanese designated health food system, the Japanese health-promoting food system addresses not only ordinary food products, but also food products in the form of tablets, capsules, etc., and comprises the three categories of designated health foods, function-labeled food products, and functional nutritional foods. Foods for special dietary uses are special-purpose food products for people who are incapable of eating ordinary meals, such as the sick, infants, and the elderly, and include food products for the sick (authorization standard type and individual evaluation type), powdered milk for pregnant and nursing women, infant formula, and food products for individuals who have difficulty swallowing.

Though not limited thereto, the composition can, for example, be used in a low-protein food product for individuals having reduced kidney function or an individual evaluation type food product for the sick, or in a function-labeled food product for healthy individuals, or individuals having kidney function indexes in the normal range or mild illness range.

One example of the food or beverage product composition is powdered infant formula. "Powdered infant formula" refers to powdered infant formula for infants 0-12 months old, follow-up milk for infants and children at least 6-9 months old (up to three years), formula for low-birthweight infants for newborns having a weight of 2,500 g or less at birth (low-birthweight infants), various types of therapeutic milk used to treat infants having pathological conditions such as milk allergy or lactose intolerance.

Examples of the food or beverage product composition include nutritional preparation food products, such as milk for pregnant and nursing mothers (powdered formulas containing a balance of nutrients needed during pregnancy and nursing) and powdered milk preparations for adults; functional nutritional foods such as nutritional supplements and liquid diets; and food products for the sick (foods for special dietary uses) such as low-phosphorus powdered milk.

Powdered formula can be produced, for example, according to the following method.

A method of producing powdered milk for infants or milk for mothers is provided, wherein powdered bacteria containing bacteria of genus *Bifidobacterium* are mixed with a prebiotic and/or powdered milk to obtain powdered milk for preventing or improving impaired renal function.

Specifically, for example, a method of producing powdered milk for fortifying mother's milk components is provided, the method including the following steps (A) through (C):

(A) culturing *Bifidobacterium* bacteria in a medium containing milk components to obtain a culture;

(B) spray-drying and/or freeze-drying the culture to obtain powdered bacteria; and (C) mixing the powdered bacteria with a prebiotic and/or powdered milk to obtain powdered milk for preventing or improving impaired renal function.

Supplement

The food or beverage product composition may also be a supplement for preventing or improving impaired renal function.

The supplement for preventing or improving impaired renal function can be produced, for example, according to the following method.

Specifically, a method of producing a supplement for preventing or improving impaired renal function is provided, the method including the following steps (A) and (B):

(A) mixing a prebiotic, *Bifidobacterium* bacteria, and an excipient to obtain a mixture; and (B) punching the mixture into tablets.

Function-Labeled Food or Beverage Product

The food or beverage product composition, etc., defined herein can also be provided or sold for special purposes (especially for health purposes) or as a food or beverage product having a labeled function.

"Labeling" refers to all actions taken in order to inform consumers of the purpose of the product, and includes all "labeling", regardless of purpose, content, label object/medium, etc., that is capable of creating an expression that will suggest or imply said purpose.

"Labeling" is preferably performed in a way such that consumers can directly recognize the abovementioned purpose. Specific examples include transferring, delivering, displaying for transferal or delivery, or importing a commercial food or beverage product or a product having the aforementioned purpose listed on the packaging; and displaying or distributing the abovementioned purpose in advertisements, price lists, and transactional documents associated with the product, or electromagnetically providing (via the Internet, etc.) said purpose in information containing the abovementioned information types.

As concerns label contents, a government-approved label (such as labels that are approved via various government-established systems, and are displayed in a form based on said approval) is preferable. The label contents are preferably appended to packaging, containers, catalogues, pamphlets, POP displays and other promotional materials at the point of purchase, other documentation, or the like.

Examples of "labeling" include labeling as a health food, functional food, food product for the sick, enteral nutrition food product, food for special dietary uses, health-promoting food, designated health food, function-labeled food product, nutritional supplement, quasi drug, or the like. Particular examples include labels approved by the Japanese Consumer Affairs Agency, such as labels approved under the designated health food system, the function-labeled food product system, and similar systems. More specific examples include labeling as a designated health food, labeling as a conditional designated health food, labeling as a function-labeled food product, labeling indicating effects upon the structure or functioning of the body, and labeling indicating reduced disease risk. Typical examples of these include labeling as a designated health food (especially labeling for health purposes) according to the Regulations for Enforcing the Japanese Promotion of Health Act (Japanese Ministry of Health, Labour and Welfare Order No. 86, 30 Apr. 2003), labeling as a function-labeled food product according to the Japanese Food Labeling Act (Act No. 70, 2013), and similar labeling.

It goes without saying that not only wording such as preventing or improving impaired renal function, but also other wording indicating effects of preventing, treating, and/or improving various diseases or symptoms associated with preventing or improving impaired renal function, are encompassed as the wording used in the labeling described above. Examples of such wording include labeling indicating various uses that will make the consumer cognizant of effects of preventing or improving impaired renal function, such as "for individuals worried about kidney function" and "for individuals worried about blood creatine levels". It is also possible to indicate effects of preventing or improving impaired renal function on the basis of the results of evaluation using new kidney function markers, such as cystatin C, and kidney function measurement methods.

Pharmaceutical, Quasi Drug

A pharmaceutical composition or quasi drug composition using the composition for preventing or improving impaired renal function (hereafter also referred to as a "pharmaceutical or other composition") can be produced by adding the composition to a known pharmaceutical or quasi drug (hereafter also referred to as a "pharmaceutical, etc."), or by mixing the composition to the ingredients of a pharmaceutical, etc., to produce a new pharmaceutical, etc.

When the composition for preventing or improving impaired renal function is used in a pharmaceutical, etc., composition, a formulation of the composition in a desired dosage form can be produced, as appropriate, according to the route of administration, such as oral or non-oral. While there is no particular limitation upon the dosage form, examples in the case of oral administration include solid formulations such as powders, granules, tablets, lozenges, and capsules; and liquid formulations such as solutions, syrups, suspensions, and emulsions. Examples of formulations in the case of non-oral administration include suppositories, sprays, inhalers, ointments, patches, and injections. It is preferable to prepare a dosage form for oral administration. The formulation can be produced via a known method, as appropriate, according to the dosage form.

When producing the formulation, a formulation carrier may be added, as appropriate. In addition to the composition for preventing or improving impaired renal function, excipients, pH adjusters, colorants, taste masking agents, and other components ordinarily used to prepare drug formulations can also be used. Components, known or discovered in the future, that have effects of preventing, improving, and/or treating disease or symptoms may also be concomitantly used, according to purpose, as long as the effects are not negatively affected.

Various organic and inorganic carriers can be used as a formulation carrier according to the dosage form. Examples of carriers in the case of solid formulations include excipients, binders, disintegrants, lubricants, stabilizers, and taste and odor masking agents.

Examples of excipients include lactose, sucrose, glucose, and sugar derivatives such as mannitol and sorbitol; cornstarch, potato starch, and starch derivatives such as alpha-starch, dextrin, and carboxymethyl starch; cellulose derivatives such as crystalline cellulose, hyhydroxypropyl cellulose, hydroxypropyl methyl cellulose, carboxymethyl cellulose, and calcium carboxymethyl cellulose; gum arabic; dextran; pullulan; silicate derivatives such as soft silicic anhydride, synthetic aluminum silicate, and magnesium aluminometasilicate; phosphate derivatives such as calcium phosphate; carbonate derivatives such as calcium carbonate; and sulfate derivatives such as calcium sulfate.

Examples of binders include gelatin, polyvinylpyrrolidone, macrogol, and the like, in addition to the excipients listed above.

Examples of disintegrants include chemically modified starch and cellulose derivatives such as croscarmellose sodium, sodium carboxymethyl starch, and cross-linked vinylpyrrolidone, in addition to the excipients listed abovementioned.

Examples of lubricants include talc; stearic acid; metal stearates such as calcium stearate and magnesium stearate; colloidal silica; waxes such as pea gum and spermaceti; boric acid; glycol; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicates such as silicic anhydride and silicic acid hydrate; and starch derivatives.

Examples of stabilizers include paroxybenzoate esters such as methylparaben and propylparaben; alcohols such as chlorobutanol, benzyl alcohol, and phenethyl alcohol; benzalkonium chloride; acetic anhydride; and sorbic acid.

Examples of taste and odor masking agents include sweeteners, acidifying agents, and fragrances.

Examples of carriers used in liquid preparations for oral administration include solvents such as water, taste and odor masking agents, etc.

The *Bifidobacterium breve* MCC1274 (FERM BP-11175) content of the pharmaceutical, etc., composition can be freely set as long as the effects are not negatively affected. The pharmaceutical, etc., composition especially preferably has a *Bifidobacterium breve* MCC1274 (FERM BP-11175) content of $1\times10^3$ to $1\times10^{12}$ cfu/g with respect to the final pharmaceutical, etc., composition. The daily dosage is at least $1\times10^3$ cfu/day, more preferably $1\times10^6$ cfu/day, more preferably $1\times10^8$ cfu/day, more preferably $2\times10^{10}$ cfu/day or more. It is especially preferable that one package contain $10^6$ to $10^{12}$ cfu of *Bifidobacterium breve* MCC1274 (FERM BP-11175).

Animal Feed

An animal feed using the composition for preventing or improving impaired renal function can be prepared by adding the composition to a known animal feed, or by mixing the composition with the raw materials of an animal feed to produce a new animal feed.

Examples of animal feed raw materials used when the composition for preventing or improving impaired renal function is used in an animal feed include grains such as maize, wheat, barley, and rye; brans such wheat bran, barley bran, rice bran, and defatted rice bran; production meal such as corn gluten meal and corn germ meal; animal-based feed ingredients such as skimmed powdered milk, whey, fish meal, and bone meal; yeasts such as brewer's yeast; mineral-based feed ingredients such as calcium phosphate and calcium carbonate; fats and oils; amino acids; and sugars. Examples of the form of the animal feed include animal feeds for pets (pet food, etc.), livestock feed, and fish feed.

The *Bifidobacterium breve* MCC1274 (FERM BP-11175) content in the animal feed can be freely set according to weight, etc., as long as the effects are not negatively affected. The *Bifidobacterium breve* MCC1274 (FERM BP-11175) content of the animal feed is preferably $1\times10^3$ to $1\times10^{12}$ cfu/g with respect to the final composition of the animal feed. The daily dosage is at least $1\times10^3$ cfu/day, more preferably $1\times10^6$ cfu/day, more preferably $1\times10^8$ cfu/day, more preferably $2\times10^{10}$ cfu/day or more.

EXAMPLES

Hereafter, the present invention will be described in greater detail on the basis of examples. The examples described hereafter are merely examples of representative examples of the present invention, and the scope of the present invention will not be narrowly construed on the basis thereof.

Example 1

<Production of Test Materials>

Fermented milk containing *Bifidobacterium breve* MCC1274 (FERM BP-11175) was produced according to the following procedure.

First, the milk feedstock was mixed with water and other components as necessary, and homogenized and pasteurized according to ordinary methods. Freeze-dried *Bifidobacterium breve* MCC1274 (FERM BP-11175) and a lactic acid bacteria starter were added (inoculated) to the pasteurized, sterilized milk preparation, the mixture was kept at a specific fermentation temperature to cause fermentation, and, once the target pH value had been reached, the formed curds were broken via agitation, and cooled to 10° C. or less to produce fermented milk, which was used as a test material.

<Test Subject>

Healthy individuals (BMI: at least 25 to less than 30) at least 20 and less than 65 years of age at the time consent was obtained were registered as test subjects for a clinical trial. Body composition measurement, blood testing, and physician interviews were then used to select 70 individuals passing all of the following exclusion criteria (1) through (6), who were the test subjects. The average age of the test subjects was 47.6±8.6 years.

(1) Individuals having a medical history of serious disease, etc.

(2) Individuals receiving drug therapy for lifestyle diseases (diabetes, hypertension, dyslipidemia)

(3) Individuals having drug allergies or serious food allergies (4) Individuals who are pregnant, intend to become pregnant during the test period, or nursing (5) Heavy smokers, heavy consumers of alcohol (6) Individuals judged unsuitable as test subjects by the chief investigator or assistant investigator on the basis of subject background, physical findings, interview results, etc.

Test Method

After a two-week pre-trial observation period, the test subjects consumed one dose of the test material daily after meals, regardless of time of day, for a continuous 12-week period. The amount of live *Bifidobacterium breve* MCC1274 (FERM BP-11175) in the test material was at least 100 million per day (dose). In other words, daily consumption was at least 100 million live *Bifidobacterium breve* MCC1274 (FERM BP-11175) bacteria.

The blood of the test subjects was measured before consumption (baseline: week 0) and on week 12 to measure blood creatinine concentration (mg/dL). One subject voluntarily dropped out after the trial had begun. Subjects not meeting pre-established criteria (i.e., less than 80% consumption of the test material, patients not complying with drug consumption and prohibited foods, and other individuals demonstrating severe violations or deviations from the trial plan) were excluded from measurement; there were no such subjects in this trial. Accordingly, the 69 test subjects who completed the trial were analyzed.

Results

Blood creatinine level measurement results for week 0 and week 12 are shown in table 1.

TABLE 1

|  | Week 0 | Week 12 |
|---|---|---|
| Blood creatinine level (mg/dl) | 0.85 ± 0.13 | 0.82 ± 0.15* |

Results expressed in terms of average ± standard deviation.
*Comparison to value of n < 0.05 vs week 0

A t test revealed a significant reduction in blood creatinine levels from the baseline at week 12. This suggests prevention or improvement of impaired renal function.

Example 2

Production of Test Materials

A liquid culture of *Bifidobacterium breve* MCC1274 (FERM BP-11175) was concentrated, then freeze-dried to obtain powdered freeze-dried live bacteria. The powdered freeze-dried live bacteria was mixed with an excipient and filled into capsules to obtain a test material.

Test Subject

Healthy individuals (BMI: at least 25 to less than 30) at least 20 and less than 65 years of age at the time consent was obtained were registered as test subjects for a clinical trial. Body composition measurement, blood testing, and physician interviews were then used to select 40 individuals passing all of the following exclusion criteria (1) through (7), who were the test subjects. The average age of the test subjects was 45.4±9.8 years.

(1) Individuals receiving treatment for serious disease, etc., or having a medical history of serious disease, etc.

(2) Individuals suffering from and taking drugs for gastric disease (3) Individuals receiving drug therapy for lifestyle diseases (diabetes, hypertension, dyslipidemia)

(4) Individuals having a medical history of drug allergies or serious food allergies (5) Individuals who are pregnant, intend to become pregnant during the test period, or nursing (6) Heavy smokers, heavy consumers of alcohol, individuals having irregular lifestyle habits (7) Individuals judged unsuitable as test subjects by the chief investigator or assistant investigator on the basis of subject background, physical findings, interview results, etc.

Test Method

After a two-week pre-trial observation period, the test subjects consumed one dose of the test material daily along with water or the like within 30 minutes after meals for a continuous 12-week period. In other words, daily consumption was at least 200 million live *Bifidobacterium breve* MCC1274 (FERM BP-11175) bacteria.

The blood of the test subjects was measured before consumption (baseline: week 0) and on week 12 to measure blood creatinine concentration (mg/dL). Subjects not meeting pre-established criteria (i.e., less than 80% consumption of the test material, patients not complying with drug consumption and prohibited foods, and other individuals demonstrating severe violations or deviations from the trial plan) were excluded from measurement; there were no such subjects in this trial. Accordingly, the 40 test subjects who completed the trial were analyzed.

Results

Blood creatinine level measurement results for week 0 and week 12 are shown in table 2.

TABLE 2

|  | Week 0 | Week 12 |
|---|---|---|
| Blood creatinine level (mg/dl) | 0.87 ± 0.15 | 0.85 ± 0.14 |

Results expressed in terms of average ± standard deviation.

A tendency toward reduced blood creatinine level from the baseline at week 12 was observed. This suggests prevention or improvement of impaired renal function.

Production examples

Production examples of pharmaceutical compositions and food product compositions for preventing or improving impaired renal function will be described hereafter.

Production Example 1

*Bifidobacterium breve* MCC1274 (FERM BP-11175) is added to 3 mL MRS liquid medium and anaerobically cultured for 16 hours at 37° C., after which the culture liquid is concentrated and freeze-dried to obtain powdered freeze-dried cells (powdered bacteria). The powdered bacteria, whey protein concentrate (WPC), and prebiotics (lactulose, raffinose, and galactooligosaccharide) is homogeneously mixed to obtain a composition. 20 g of the composition is dissolved in 200 g water to obtain a composition for preventing or improving impaired renal function. The composition can be administered to prevent or improve impaired renal function.

Production Example 2

*Bifidobacterium breve* MCC1274 (FERM BP-11175) is added to 3 mL MRS liquid medium and anaerobically cultured for 16 hours at 37° C., after which the culture liquid is concentrated and freeze-dried to obtain powdered freeze-dried cells (powdered bacteria). The powdered bacteria, dried powdered milk protein concentrate (MPC 480, produced by Fonterra; protein content: 80 mass %; casein protein: whey protein=approx. 8:2), and prebiotics (lactulose, raffinose, and galactooligosaccharide) are homogeneously mixed to obtain a composition. 20 g of the composition is dissolved in 200 g water to obtain a composition for preventing or improving impaired renal function. The composition can be administered to prevent or improve impaired renal function.

Production Example 3

*Bifidobacterium breve* MCC1274 (FERM BP-11175) is added to 3 mL MRS liquid medium and anaerobically cultured for 16 hours at 37° C., after which the culture liquid is concentrated and freeze-dried to obtain powdered freeze-dried cells (powdered bacteria). Next, prebiotics (lactulose, raffinose, and galactooligosaccharide) and crystalline cellulose are introduced into an agitator granulator and mixed. Purified water is then added to form granules, and the granules are dried to obtain granules (a pharmaceutical composition) containing bacteria extract components, prebiotics, and an excipient. The granules can be administered to prevent or improve impaired renal function.

Production Example 4

A method of producing fermented milk containing added *Bifidobacterium breve* MCC1274 (FERM BP-11175) will be described hereafter.

First, the milk feedstock is mixed with water and other components as necessary, and preferably homogenized and pasteurized. The homogenization and pasteurization can be performed according to ordinary methods. A lactic acid bacteria starter is added (inoculated) to the pasteurized, sterilized milk preparation, and the mixture is kept at a specific fermentation temperature to cause fermentation and obtain a fermented product. The fermentation forms curds.

Lactic acid bacteria ordinarily used in yogurt production, such as *Lactobacillus bulgaricus, Lactococcus lactis*, and *Streptococcus thermophilus*, can be used as the lactic acid bacteria starter. Once the target pH value is reached, the formed curds are broken via agitation and cooled to 10° C. or less to obtain a fermented product. Cooling to 10° C. or less makes it possible to reduce the activity of the lactic acid bacteria and suppress acid generation.

Next, the fermented product obtained in the fermentation process is heat-treated to obtain a heated fermented product (heat-treated fermented product). Suitably heating the fermentation product makes it possible to suppress acid generation by the lactic acid bacteria in the heated fermentation product. As a result, it is possible to suppress reductions in pH during the subsequent production process and/or storing the Bifidobacteria-containing concentrated fermented milk, with the result that it is possible to increase the Bifidobacteria survival rate.

Next, *Bifidobacterium breve* MCC1274 (FERM BP-11175) and prebiotics (lactulose, raffinose, and galactooligosaccharide) is added to the heated fermented product obtained from the heat treatment process. The amount of added *Bifidobacterium breve* MCC1274 (FERM BP-11175) is preferably $1\times10^7\times$ to $1\times10^{11}$ cfu/ml, more preferably $1\times10^8$ to $1\times10^{10}$ cfu/ml. If the *Bifidobacterium breve* MCC1274 (FERM BP-11175) are dead, cells/mL can be substituted for cfu/mL.

*Bifidobacterium breve* MCC1274 (FERM BP-11175) and prebiotics are added to the heated fermented product, which is then concentrated. The concentration process can be performed using a known concentration method, as appropriate. For example, centrifugation or membrane separation can be used. In centrifugation, the whey in the concentrated product (heated fermented product containing added Bifidobacteria and prebiotics) is removed, thereby yielding Bifidobacteria- and prebiotics-containing concentrated fermented milk having an increased solids concentration.

The fermented milk obtained as described above can be administered to prevent or improve impaired renal function.

Production Example 5

A method of producing a powdered milk preparation containing added *Bifidobacterium breve* MCC1274 (FERM BP-11175) will be described hereafter.

10 kg desalinated cow's milk whey protein powder (produced by Milei), 6 kg powdered cow's milk casein (produced by Fonterra), 48 kg lactose (produced by Milei), 920 g of a mineral mixture (produced by Tomita Pharmaceutical Co., Ltd.), 32 g of a vitamin mixture (produced by Tanabe Pharmaceuticals), 500 g lactulose (produced by Morinaga Milk Industry), 500 g raffinose (produced by Nippon Beet Sugar Mfg. Co., Ltd.), and 900 g galactooligosaccharide (produced by Yakult Pharmaceutical Industry Co., Ltd.) were dissolved in 300 kg warm water, heated and dissolved at 90° C. for 10 minutes, 28 kg of a fat preparation (produced by Taiyo Yushi Corp.) was added thereto, and the whole was homogenized. Sterilization and concentration processes were then performed, and spray drying was performed to prepare about 95 kg of a powdered milk preparation. 100 g powdered *Bifidobacterium breve* MCC1274 (FERM BP-11175) ($1.8\times10^{11}$ cfu/g, produced by Morinaga Milk Industry) triturated with starch is added thereto to prepare about 95 kg of a powdered milk preparation containing Bifidobacteria and oligosaccharides. The obtained powdered milk preparation can be dissolved in water to obtain a liquid preparation having a total solids concentration of 14% (w/v), which is the standard concentration for milk preparations, and a Bifidobacteria count of $2.7\times10^9$ cfu/100 mL.

The powdered milk preparation obtained as described above can be used to prevent or improve impaired renal function.

The invention claimed is:

1. A method of improving renal function in a subject having impaired renal function, the method comprising administering *Bifidobacterium breve* to the subject in an amount sufficient to reduce blood creatinine levels.

2. The method according to claim 1, wherein the *Bifidobacterium breve* is *Bifidobacterium breve* MCC1274 (FERM BP-11175).

3. The method of claim 1, wherein the method also results in improved glomerular function.

4. The method of claim 1, wherein the *Bifidobacterium breve* is formulated into a pharmaceutical composition.

5. The method of claim 1, wherein the *Bifidobacterium breve* is formulated into a food or beverage product.

6. A method of reducing blood creatinine levels in a subject having impaired renal function, the method comprising administering *Bifidobacterium breve* to the subject in an amount sufficient to reduce blood creatinine levels.

7. The method according to claim 6, wherein the *Bifidobacterium breve* is *Bifidobacterium breve* MCC1274 (FERM BP-11175).

8. The method of claim 6, wherein the method also results in improved glomerular function.

9. The method of claim 6, wherein the *Bifidobacterium breve* is formulated into a pharmaceutical composition.

10. The method of claim 6, wherein the *Bifidobacterium breve* is formulated into a food or beverage product.

* * * * *